(12) United States Patent  (10) Patent No.: US 7,618,441 B2
Groiso  (45) Date of Patent: Nov. 17, 2009

(54) BONE STAPLE AND METHODS FOR CORRECTING SPINE DISORDERS

(76) Inventor: Jorge Abel Groiso, Arenales 2245 1°, Capital Federal, Buenos Aires (AR)

( * ) Notice: Subject to any disclaimer, the term of this patent is extended or adjusted under 35 U.S.C. 154(b) by 516 days.

(21) Appl. No.: 11/385,863

(22) Filed: Mar. 22, 2006

(65) Prior Publication Data

US 2006/0167459 A1    Jul. 27, 2006

Related U.S. Application Data

(60) Continuation-in-part of application No. 10/924,900, filed on Aug. 25, 2004, which is a division of application No. 10/051,156, filed on Jan. 22, 2002, now Pat. No. 6,966,911.

(51) Int. Cl.
*A61B 17/70* (2006.01)
(52) U.S. Cl. .................. 606/248; 606/279; 606/301; 606/75
(58) Field of Classification Search .............. 606/75, 606/76, 78, 77, 219, 282, 284, 285, 299, 606/324, 331, 248, 279, 301
See application file for complete search history.

(56) References Cited

U.S. PATENT DOCUMENTS

| 5,662,655 A | * | 9/1997 | Laboureau et al. | 606/75 |
| 5,785,713 A | * | 7/1998 | Jobe | 606/75 |
| 6,325,805 B1 | * | 12/2001 | Ogilvie et al. | 606/75 |
| 6,921,403 B2 | | 7/2005 | Cragg et al. | 606/86 |
| 2005/0171539 A1 | | 8/2005 | Braun et al. | 606/61 |

* cited by examiner

*Primary Examiner*—Pedro Philogene
(74) *Attorney, Agent, or Firm*—Pillsbury Winthrop Shaw Pittman LLP

(57) ABSTRACT

A method and staple for correcting an abnormally curved bone, such as a spinal column having a concave side and a convex side, the method comprising providing a staple having a central portion and a pair of legs with a first memorized shape and a second deformed shape and implanting the staple, in the second shape, at the convex side of the spinal column in a manner that the legs extend close to the concave side, such that the legs exert a distraction force at the concave side of the spinal column.

14 Claims, 10 Drawing Sheets

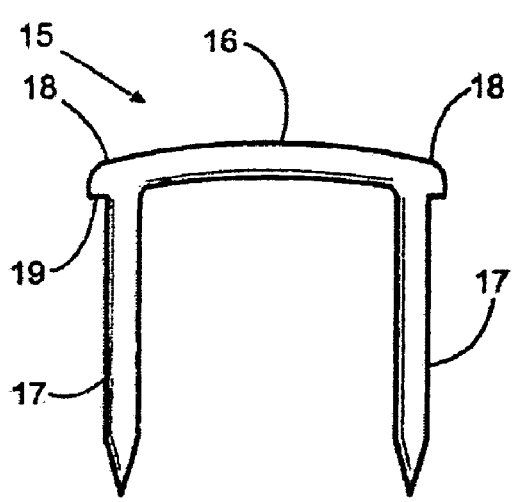
Fig.8
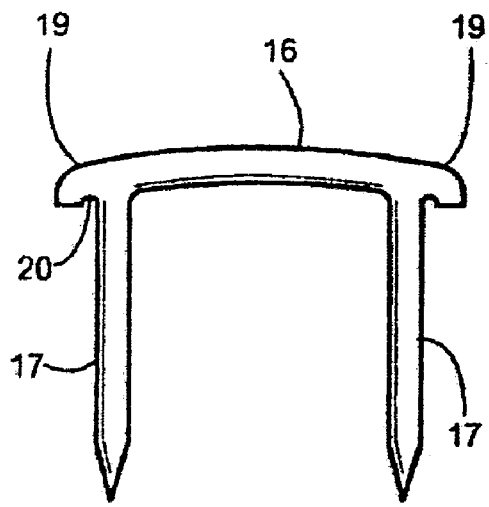
Fig.9
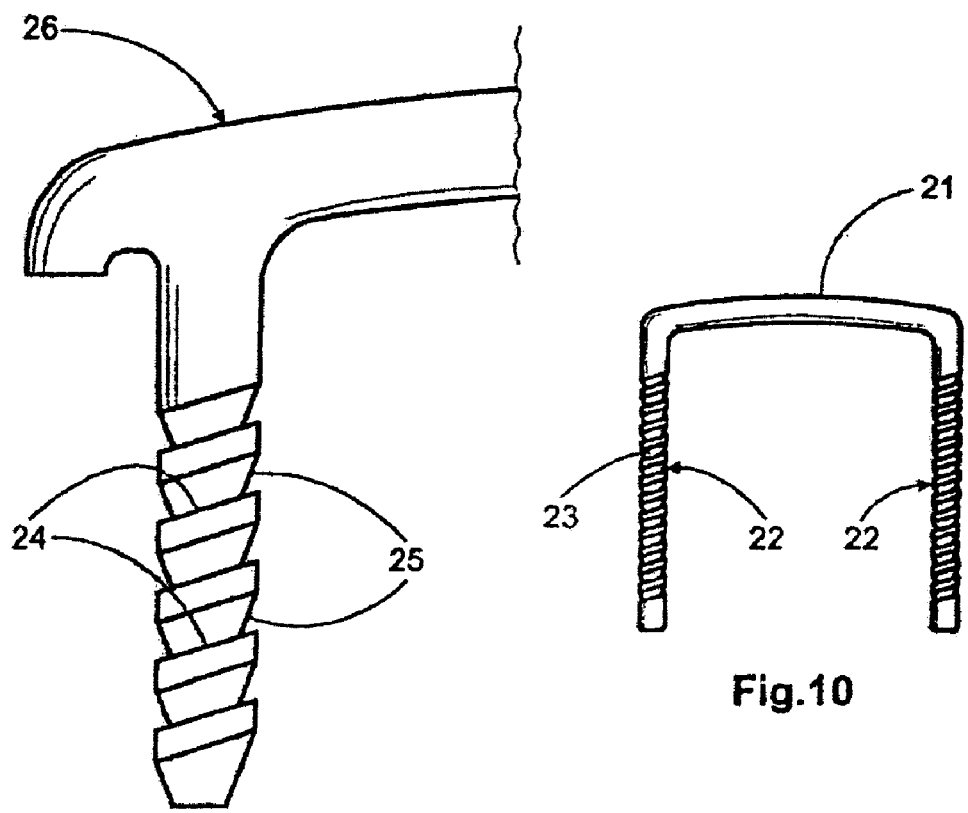
Fig.11
Fig.10

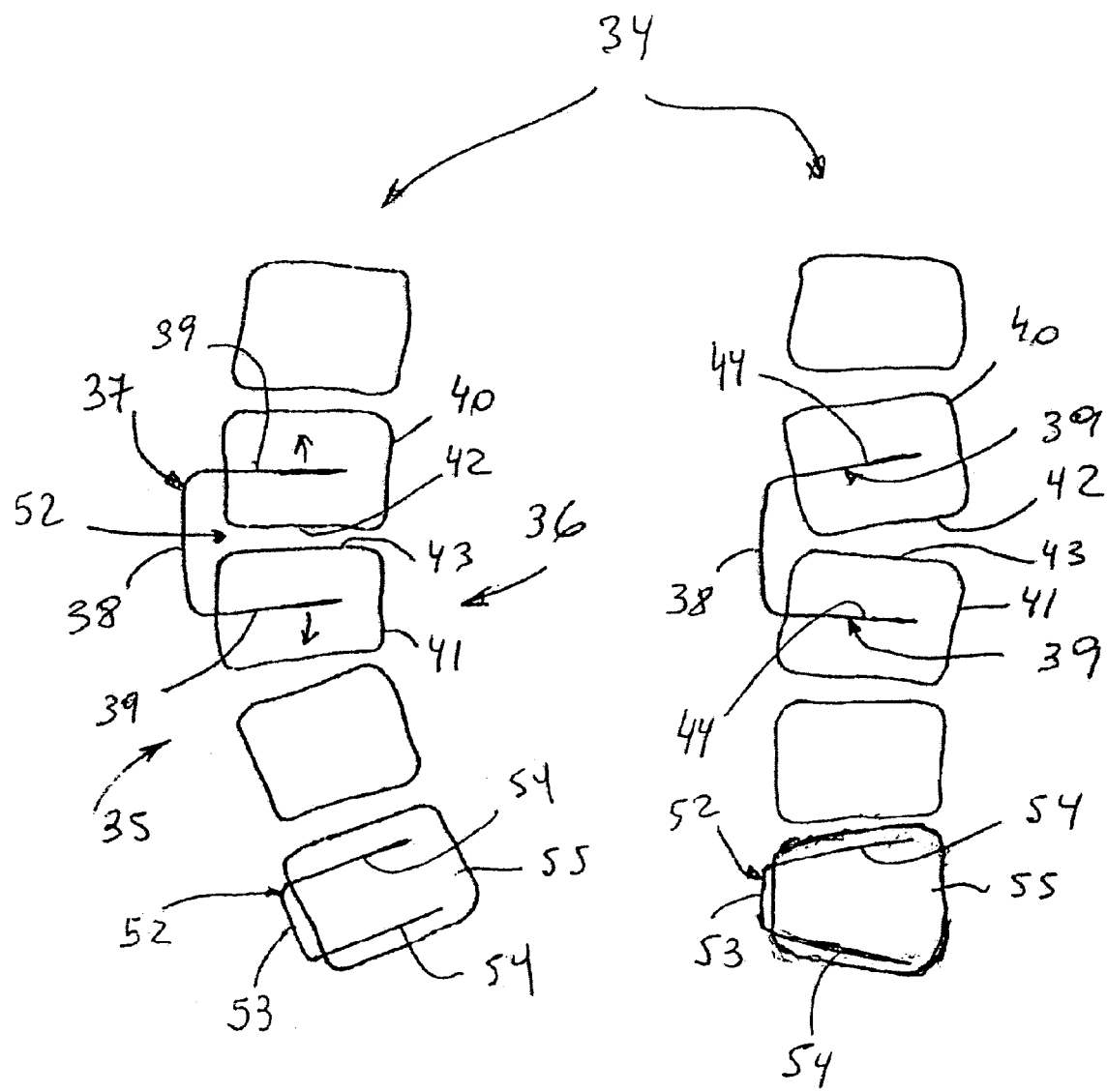
Fic. 16   Fic. 17

BONE STAPLE AND METHODS FOR CORRECTING SPINE DISORDERS

CROSS-REFERENCE TO RELATED APPLICATIONS

This application is a continuation-in-part of U.S. patent application Ser. No. 10/924,900, filed Aug. 25, 2004, which is a divisional of U.S. patent application Ser. No. 10/051,156, filed Jan. 22, 2002, now granted U.S. Pat. No. 6,966,911, issued on Nov. 22, 2005, all of which are incorporated herein by reference.

BACKGROUND OF THE INVENTION

1. Field of the Invention

The present invention relates to the medical field and particularly to orthopaedics and traumatology for the correction of limb bone deformities, disorders and deficiencies. More particularly, the invention relates to an implant or staple and method for repairing bones and/or correcting limb inequality and most preferably the invention relates to methods and staples for correcting bone deficiencies such as abnormal curvatures by suppressing and/or inducing the growth of the bone mass and/or the epiphyseal plate in the bone. Even most particularly the invention relates to a distraction staple and method for correcting abnormally curved spinal columns by distracting the vertebrae at the concave side of the column and promoting the growth of the end plate or epiphyseal plate at the concave side. Additionally, the invention relates to staples with enhanced osseous integrating means capable of being easily removed from the bone even once integrated. Furthermore, the invention relates to staples for preventing the perichondrium and the periosteal vascular ring from damage when installing the staple into the bone.

While more specific reference to disorders in the spinal column control and/or will be made in the present disclosure and drawings, the bone implant and methods of the invention are not restricted to this specific application but they may be applied to any other field where a prosthesis, a fixation device, a correction device, etc. is to be secured into a bone, proximal bones or a broken bone for correction and/or reparation purposes. In addition, the term "patient" is applicable either to animals or human beings.

2. Description of the Prior Art

Length discrepancies and angular deformities of the limbs are quite frequent among children and provoked by several causes such as congenital, post-trauma, post-infection, oncologic causes, etc. The need exists for correcting these abnormalities because of function and aesthetic reasons. The treatment of some of these childhood deformities is based on the concept of mechanically suppressing growth.

Bone staples are well known in the orthopaedics and traumatology, such as in techniques for correcting angular deviations of limbs, genu valgum for example, by unilateral restriction of the growth plate.

For correcting angular deviations the mechanical suppression can be obtained by temporary using metal staples across the growth plate, at unilateral locations, at the convex side of the deformity, for example. The staples are removed once the correction has been reached.

For correcting length abnormalities, the lengthening of the bone is obtained by using an external fixator and the shortening of the limb is obtained by arresting or suppressing the growth plate at even locations around the bone.

The technique of mechanical suppression by temporary using an external fixator is carried out by installing the fixator in the limb, on the concave bone side, for producing a slow stretching of the growth plate. This mechanical technique is known as epiphyseal distraction.

More precisely, epiphyseal distraction is a surgical technique that is widely used to lengthen an abnormal bone or correct physeal deviations prior to growth plate closure. This technique, also called "chondrodiatasis", involves slow, gradual, symmetric distraction of the growth plate. The term "hemichondrodiatasis", on the other hand, is used to refer to the technique of asymmetric distraction of the growth plate for correction of epiphyseal-diaphyseal deviations.

Since the use of external fixators for the above described mechanical suppressing techniques has shown to be expensive as well as traumatic and cumbersome for the patient, and the fixator leaves unsightly scars, the use of this device has not widely and intensively imposed. It would be desirable to use staples for these techniques, however, the staples are affected by several disadvantages and drawbacks that caused them to be not widely imposed in the medical field.

As it was stated above, angular deviations or deformities and length discrepancies of the limbs, for example, are often treated with staples. After staples are placed across a growth plate, further growth of this plate increases the pressure on the inner surfaces of the staple legs. This increased pressure, which has been measured about 1 Mpa, slows bone growth within and near the staple, i.e. in the region between the legs, and, simultaneously, forces the staple legs apart. This pressure from the cartilage plate, together with the legs moving away from each other, causes the legs to be extruded and expelled out from the bone thus loosing the grip in the bone.

Another drawback the physicians have found with the use of staples is that the same do not work satisfactorily because the bone growth is not restarted afterwards, thus producing the appearance of opposite deformity due to the constant growth of the cartilage of the side that was not operated upon. An explanation for this effect is that, presumably, a damage is inflicted on the perichondrium or the perichondrial vessels when the staples are inserted into physis. Generally, the staples are provided with reinforcing squares. at the inner side thereof, that is at the inner corners formed by the connection between the cross bar and legs. As the staple is hammered up to abutting the external surface of the bone, the reinforcements, as well as the flat bridge or cross bar enter into contact with the growth plate and damage the perochondrium and the perichondrial vessels, this being the cause of the undesired epiphysial arrest.

As indicated above in connection with one of the drawbacks of using staples, the pressure exerted by the growing cartilage plate causes the staple legs to open, extrude and slide out of the bone. Many staples of the prior art has attempted to prevent the staple from sliding out the bone by providing the staple legs with barbs or protrusions to enhance the anchoring of the legs into the bone mass. However, when the deformation has been corrected and the temporary staple must be removed from the bone, the anchorage of the legs into the growing bone mass, desired at the time the stable must be retained into the bone, is a bar or obstacle at the time the staple must be removed. In effect, this firm osseous anchorage prevents the staple from being easily removed by normal forces and operations.

Another aspect related to the bone malformations or disorders is the correction of abnormal curvatures in spinal columns, such as scoliosis. There are several devices, systems, implants and staples for connecting to the vertebrae to exert a force or combination of forces to urge the column and bring the same as close as possible into its normal curvature.

U.S. Pat. No. 6,325,805 to Ogilvie, et al. discloses a shape memory alloy staple comprising a cross bar with two or more prongs having a memorized shape wherein the prongs are angled towards one another and a deformed shape wherein the prongs are substantially parallel. This staple is for implanting in a couple of proximal vertebrae with said prongs in said deformed shape and the cross bar spanning the intervertebral disc with the purpose of exerting a compression force on the vertebrae. The fact of retaining a portion of the spine while permitting the growth of another part may operate successfully to correct the abnormal curvature of the spine, the final result is that the entire growth of the column is restricted and the column results, after the period of time involved in the treatment, shorter that it should be after the same period of time without any retention.

In order to prevent the restriction on the normal growth of the spine, other systems have been based in the distraction of the vertebrae instead of compressing the same. U.S. Pat. No. 6,921,403 to Cragg, et al. discloses a method and apparatus for spinal distraction and fusion wherein an axial bore is created in the spine up to the targeted vertebrae to be treated. An axially-extending rod with appropriate threads is inserted into the axial bore and the rod is extended to increase the distance between the two proximal vertebrae. While no compression is made the distraction is obtained by employing complex, cumbersome and dangerous systems.

U.S. patent application Ser. No. 10/768,797, published under No. US 2005/0171539 A1, to Braun, et al. discloses an implant simpler than the above Cragg's apparatus. Braun discloses a flexible body that is fixed at the ends thereof to respective fasteners which in turn are fixed to two proximal vertebrae with the flexible body extending intervertebrally between the two vertebrae. Before connecting to the two fasteners the flexible body is compressed in order to exert a distraction force between the fasteners. Since the fasteners are fixed to the vertebrae with the flexible body in said compressed state, the fasteners will transmit to the vertebrae the corresponding distraction force exerted by the flexible body. While this system is simple, it consists of at least three parts which is a drawback when it is working in a most sensitive area like the spinal column and, particularly when as smallest as possible tools are desired to be employed in the intervention. In addition, the use of fasteners, such as screws, is less and less preferred for the patient security. Another drawback of Bauer's system, which is not less important, is that the implant is attachable to the concave side of the spinal column with the undesired result that not only the concave side is distracted but also the convex side. In deed the growth of the vertebrae end plates at the convex side are inconveniently promoted with the final result of an abnormally elongated spine.

It would be therefore desirable and convenient to have a staple capable of being easily installed and implanted as well as a method for effectively correcting a spinal column that is out of its normal curvature without restricting and/or abnormally affecting the natural growth of the vertebrae.

SUMMARY OF THE INVENTION

It is therefore an object of the present invention to provide an expansion bone staple for correcting bone deficiencies by controlling the growth of the epiphyseal plate, the staple comprising:

a shape memory material body comprising a cross bar and at least two legs extending from the cross bar and normally diverging from each other, wherein the legs define spring legs tending to expand apart from each other when subject to a compression force, whereby when the staple is introduced into a bone with each leg at each side of the epiphyseal plate under a compression force bringing the legs to be closer than in a normal position the legs exert a expansion force for lengthening the epiphyseal plate while the cross bar keeps a normal length thereof forming a tether for a periphery of the epiphyseal plate, thus causing the epiphyseal plate to growth around a focus.

It is still another object of the present invention to provide a method for installing said expansion staple into a bone, for correcting bone deficiencies by controlling the growth of the epiphyseal plate, the method comprising:

i. providing said staple with the legs normally diverging from each other, ii. applying a compression force to the legs and bringing the legs into a substantially parallel position, and ii. nailing the staple into the bone with at least one leg nailed at each side of the epiphyseal plate, whereby the staple will be retained into the bone with the legs exerting an expansion force over the epiphyseal plate while the cross bar will exert a suppression effect on the periphery of the epiphyseal plate.

It is a further object of the present invention to provide an abutting bone staple for correcting bone deficiencies by controlling the growth of the epiphyseal plate, the staple comprising:

a body comprising a cross bar and at least two legs extending from the cross bar, wherein the cross bar extends beyond a corner joint with the legs and forms stop means for abutting the bone, the cross bar defining an arc shape extending between the legs and at a level higher than the stop means, whereby when the staple is installed into the bone the arc shaped cross bar remains spaced apart from the epiphyseal plate.

It is even another object of the present invention to provide a method for installing the above mentioned abutting bone staple, for correcting bone deficiencies by controlling the growth of the epiphyseal plate, the method comprising:

i. providing said staple, ii. placing the staple with the cross bar spanning across the epiphyseal plate, and ii. nailing the staple into the bone with at least one leg nailed at each side of the epiphyseal plate, whereby the stop means abut against the bone at each side of the epiphyseal plate and the arc shaped cross bar remains spaced apart from the epiphyseal plate.

It is even another object of the present invention to provide a screw bone staple for repairing bones and correcting bone deficiencies, the staple comprising:

a body comprising a cross bar and at least two legs extending from the cross bar, wherein each leg includes an helical thread designed for anchoring into the bone, the cross bar being designed to be cut whereby once the bone deficiency is overcome and the staple is anchored the cross bar is cut and each leg is unscrewed and removed from the bone.

It is even another object of the present invention to provide a method for installing and removing the above mentioned screw bone staple., for repairing bones and correcting bone deficiencies, the method comprising:

i. providing said staple, ii. installing the staple by inserting the legs of the staple into the bone, iii. waiting for a period of time enough for repairing the bone or correcting the bone deficiency, wherein the staple legs are anchored into the bone, iv. cutting the cross bar in a location between the legs, and v. removing each leg from the bone by gripping and unscrewing the leg from the bone.

It is a further object of the present invention to provide a method and staple for correcting a bone that is curved out of its natural curvature and has at least one concave side and at least one convex side, the method comprising:

providing a distraction implant made of a shape memory material and having a central portion and at least two opposite legs, with the implant having a first shape, in a memorized state, and a second shape, in a deformed state, wherein the legs extend diverging from each other in said first shape, bringing the implant into said second shape, implanting the distraction implant in the bone by connecting the central portion to the convex side of the bone with the legs extending in the second shape and with at least a portion thereof close to the concave side, whereby the legs, in the deformed state, are fixed to the bone and the legs exert a distraction force in the bone at said concave side.

It is still another object of the present invention to provide a distraction implant for correcting a bone that is curved out of its natural curvature and has at least one concave side and at least one convex side, wherein the implant is at least partially made of a shape memory material and has a central portion and at least two opposite legs, with the implant having a first shape, in a memorized state, and a second shape, in a deformed state, wherein the legs extend diverging from each other in said first shape, and each leg has a length enough to extend from the convex side and close to said concave side of the bone.

It is a further object of the present invention to provide a method and staple for correcting an abnormally curved spinal column having a concave side and a convex side, the method comprising providing a staple having a central portion and a pair of legs with a first memorized shape and a second deformed shape and implanting the staple, in the second shape, at the convex side of the spinal column in a manner that the legs extend close to the concave side, such that the legs exert a distraction force at the concave side of the spinal column.

It is still another object of the present invention to provide a method for correcting a spinal column that is curved out of its natural curvature and has at least one concave side and at least one convex side, the method comprising:

providing a distraction implant made of a shape memory material and having a central portion and at least two opposite legs, with the implant having a first shape, in a memorized state, and a second shape, in a deformed state, wherein the legs extend diverging from each other in said first shape, bringing the implant into said second shape, implanting the distraction implant in the convex side by connecting one leg of the implant to one of two proximal misaligned vertebrae and the other leg of the implant to the other one of the proximal vertebrae with the central portion extending, at the convex side, over corresponding epiphyseal plates of each proximal vertebrae, and with the legs extending in the second shape and with at least a portion thereof close to the concave side when connected to the vertebrae, whereby the legs are fixed to the vertebrae in the deformed state with the legs exerting a distraction force over the epiphyseal plate of the vertebrae at said concave side.

It is still another object of the present invention to provide a method for correcting a spinal column that is curved out of its natural curvature and has at least one concave side and at least one convex side, the method comprising:

providing a distraction implant made of a shape memory material and having a central portion and at least two opposite legs, with the implant having a first shape, in a memorized state, and a second shape, in a deformed state, wherein the legs extend diverging from each other in said first shape, bringing the implant into said second shape, implanting the distraction implant in the convex side by connecting or inserting one leg of the implant to or into one of two proximal misaligned vertebrae and the other leg of the implant to or into the other one of the proximal vertebrae with the central portion extending, at the convex side, over corresponding epiphyseal plates of each proximal vertebrae, and with the legs extending in the second shape and with at least a portion thereof close to the concave side when connected to the vertebrae, whereby the legs are fixed to the vertebrae in the deformed state with the legs exerting a distraction force over the epiphyseal plate of the vertebrae at said concave side, and wherein the implant has said first shape at a first temperature that is a normal temperature of the spinal column and said second shape at a second temperature lower than the first temperature, and the implant is brought to said second shape by bringing the implant to said second temperature, and wherein the implant is warmed up to the first temperature, in contact with the vertebrae, whereby the legs tend to recover their first shape and exert said distraction force at the concave side in the proximal vertebrae.

It is still another object of the present invention to provide a method for correcting a spinal column that is curved out of its natural curvature and has at least one concave side and at least one convex side, the method comprising:

providing a distraction implant made of a shape memory material and having a central portion and at least two opposite legs, with the implant having a first shape, in a memorized state, and a second shape, in a deformed state, wherein the legs extend diverging from each other in said first shape, bringing the implant into said second shape, implanting the distraction implant in the convex side by connecting one leg of the implant to one of two proximal misaligned vertebrae and the other leg of the implant to the other one of the proximal vertebrae with the central portion extending, at the convex side, over corresponding epiphyseal plates of each proximal vertebrae, and with the legs extending in the second shape and with at least a portion thereof close to the concave side when connected to the vertebrae, whereby the legs are fixed to the vertebrae in the deformed state with the legs exerting a distraction force over the epiphyseal plate of the vertebrae at said concave side, and wherein each leg includes an helical thread designed for anchoring by osseous integration into the vertebra, and the central portion being designed to be cut whereby once the staple must be removed from the vertebrae the method comprises the steps of:

cutting the central portion in a location between the legs, and removing the legs from the vertebrae by gripping and unscrewing the legs.

It is even another object of the present invention to provide a distraction implant for correcting a spinal column that is curved out of its natural curvature and has at least one concave side and at least one convex side, wherein the implant is at least partially made of a shape memory material and has a central portion and at least two opposite legs, with the implant having a first shape, in a memorized state, and a second shape, in a deformed state, wherein the legs extend diverging from each other in said first shape, and the central portion has a length longer than a intervertebral distance defined between two proximal vertebrae at said convex side and each leg has a length enough to extend close to said concave side of the spine column.

The above and other objects, features and advantages of this invention will be better understood when taken in connection with the accompanying drawings and description.

BRIEF DESCRIPTION OF THE DRAWINGS

The present invention is illustrated by way of example in the following drawings wherein:

FIG. 8 shows a side elevational view of a bone staple according to another embodiment of the invention;

FIG. 9 shows a side elevational view of a bone staple according to a further embodiment of the invention;

FIG. 10 shows a side elevational view of a bone staple according to a further embodiment of the invention, including unscrewable means for enhancing the anchoring of the staple legs;

FIG. 11 shows a side elevational partially cross-section view of a further inventive bone staple including unscrewable means for enhancing the anchoring of the legs into the bone;

FIG. 16 schematically shows a spinal column affected by an abnormal curvature with the staple according to an embodiment of the invention implanted in two proximal vertebrae and with the staple in its deformed status or shape;

FIG. 17 schematically shows the spinal column of FIG. 16 as it is corrected after a period of time and with the inventive staple in its memorized status or shape, wherein the two proximal vertebrae has been brought into a new angled position to correct the abnormality;

DESCRIPTION OF THE PREFERRED EMBODIMENTS

Now referring in detail to the drawings reference will be made to several alternative staples, methods for implanting the same and applications to correct different and distinct malformations and abnormalities such as in long bones, broken bones, spinal column, etc.

Figure 1:
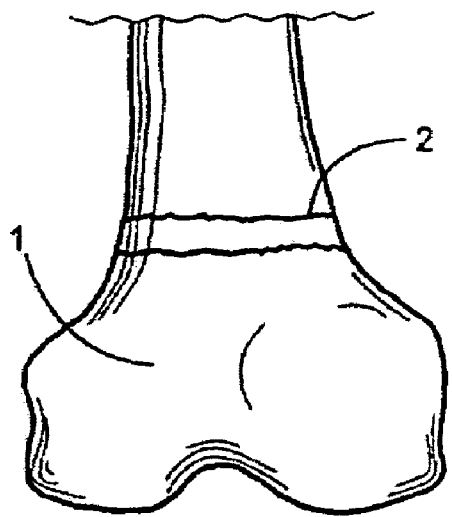
FIG. 1 shows a diagrammatic side elevation view of a femur head with a normal physis.
Figure 2:
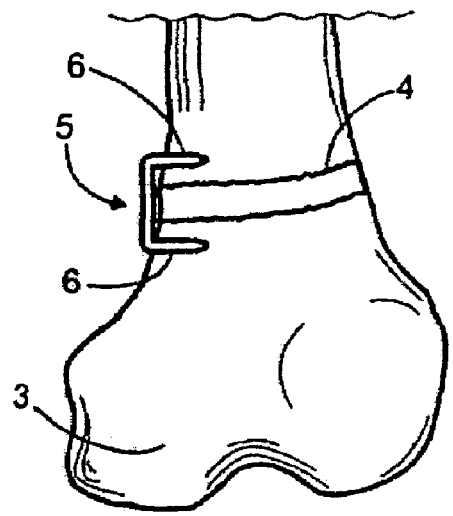
FIG. 2 shows a diagrammatic side elevation view of a femur head with an abnormal angled physis and a staple of the prior art installed into the bone for controlling the growth of the epiphyseal plate.
Figure 3:
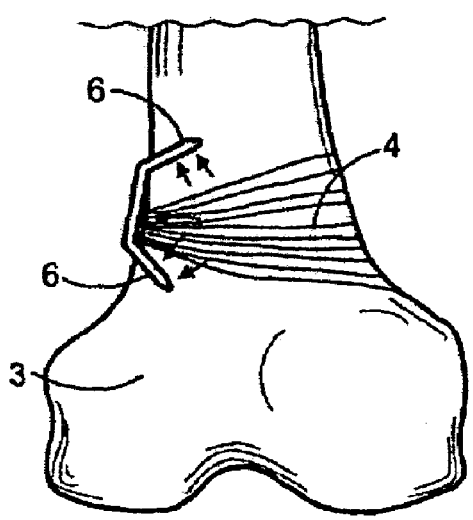
FIG. 3 shows a diagrammatic side elevation view of the femur head of FIG. 2 after a period of time has passed from the surgery, with the staple being expanded against the compression force of the staple legs.
Figure 4:
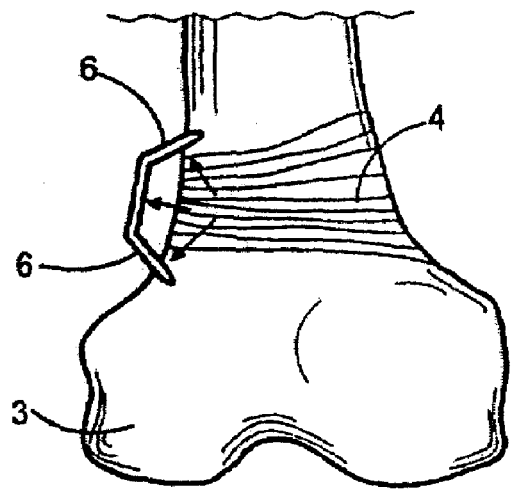
FIG. 4 shows a diagrammatic side elevation view of the femur head of FIG. 3 after a further period of time, with the staple slipped out the bone under the expansion force of the cartilage plate.

It may be seen from FIG. 1 a normal bone, particularly a femur head 1 having a normal epiphyseal or growth plate 2 whereby the femur growths normally along a normal longitudinal axis of the bone. When the bone, such as bone 3, includes an abnormal growth plate, an angled plate 4 as shown in FIGS. 2-4, for example, the bone tends to growth along a line deviated out from the normal bone axis, thus providing the bone with a convex side and a concave side. Depending of the location of this abnormalities the patient will be affected of a genu valgum or varum. FIG. 2 clearly shows that the left bottom portion or protrusion of bone 3 is larger than the right one, therefore a bottom bone (not illustrated) that is joined to bone 3, will be deviated from a common axis (see FIG. 6).

In order to suppress the growth at the left side and induce or allow the growth at the right side, a prior art staple 5 is nailed or installed in other way into the bone, with the staple legs 6 inserted at each side of plate 4 (FIGS. 2-4). During growth, plate 4 exerts an expansion force, indicated by arrows in FIGS. 3, 4, forcing legs 6 to move away from each other. These forces also extrude the legs into the bone mass. After a period of time from surgery, 5-7 months for instance, legs 6 are finally expelled from the bone and appear slipped out the bone as shown in FIG. 4, thus loosing the grip into the bone and failing in controllably suppressing the plate growth. FIGS. 3 and 4 show the bottom right side of bone end 3 having a size larger than the one illustrated in FIG. 2 because this right side has grown more than the left side thank to the suppression exerted by the staple. The growing would be completed, however, if the staple would not be expelled from the bone.

Figure 5:
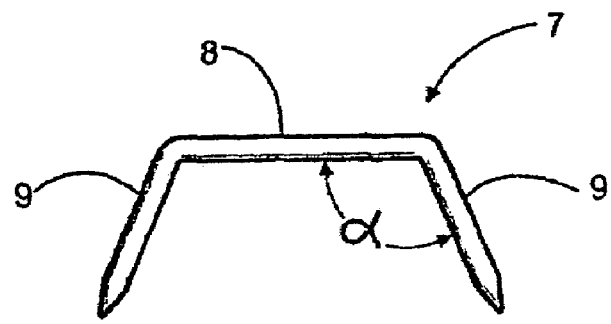
FIG. 5 shows a side elevational view of a bone staple according to a preferred embodiment of the invention.

In order to prevent the slipping out of the staple as well as for controlling the growth plate by inducing growth in the central regions thereof but arresting the periphery of same, the inventor has developed the staple of FIG. 5. The inventive staple, also named as expansion staple, indicated by generic reference number 7, is preferably for correcting bone deficiencies by controlling the growth of the epiphyseal plate, and the staple comprises a shape memory material body, preferably made of a resilient metal or alloy, and most preferably made of nitinol (NiTi alloy). The staple body includes a bridge or cross bar 8 and at least two legs 9 extending from the cross bar. Legs 9 normally diverge from each other, as shown in FIG. 5, whereby the same define spring legs that tend to keep their open or diverging normal position, or resting position, and to exert a resilient expansion force when subject to a compression force 2. Each leg normally defines an angle α of between about 91° to about 180° degrees relative to the cross bar, preferably an angle between 105° and 185°, and most preferably 135°.

Figure 6:
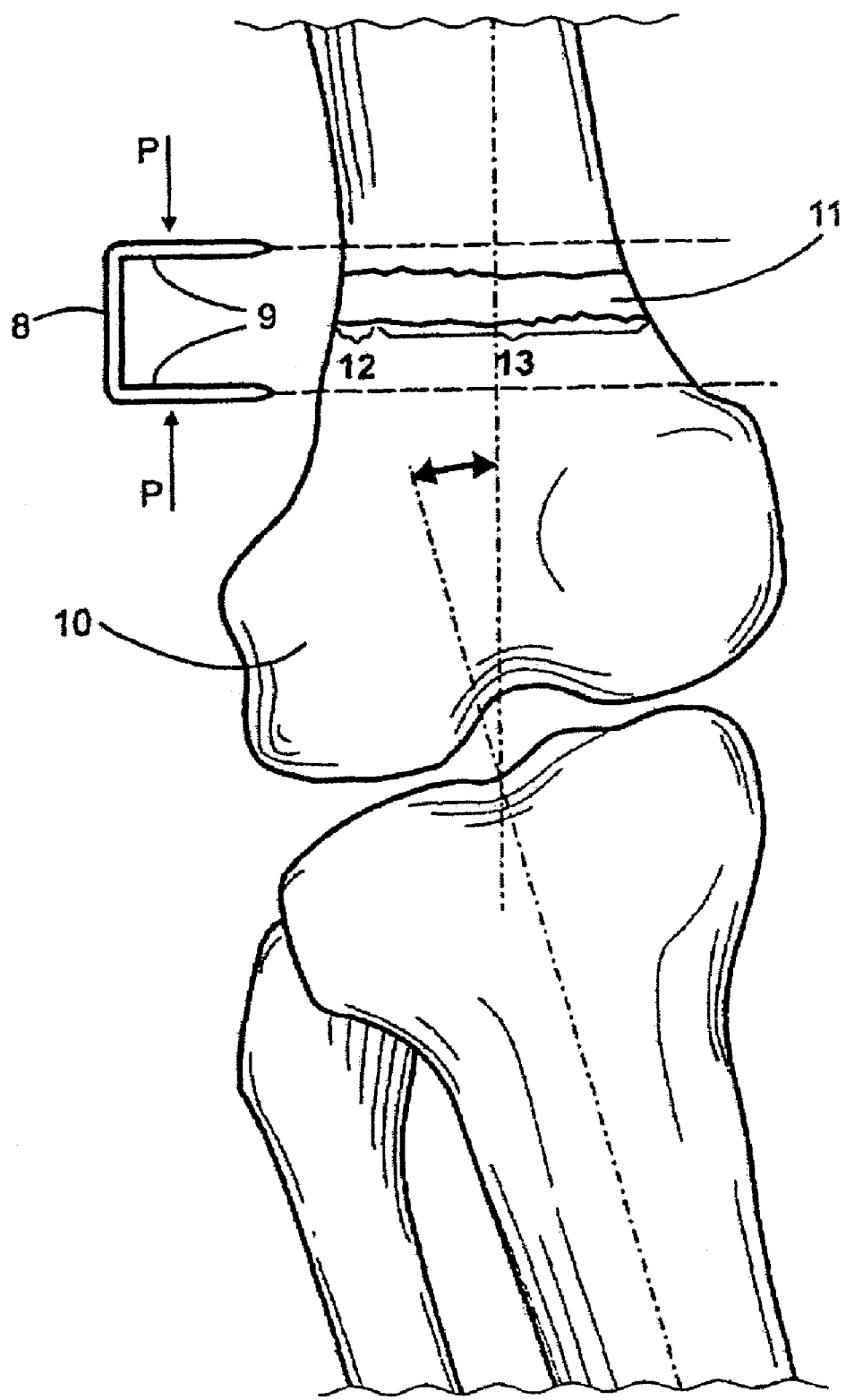
FIG. 6 is a diagrammatic side elevational view of a femur head with an abnormal growth plate and the staple of FIG. 5 with its legs brought into a parallel position under a compression force, ready to be inserted into the bone, across the plate.
Figure 7:
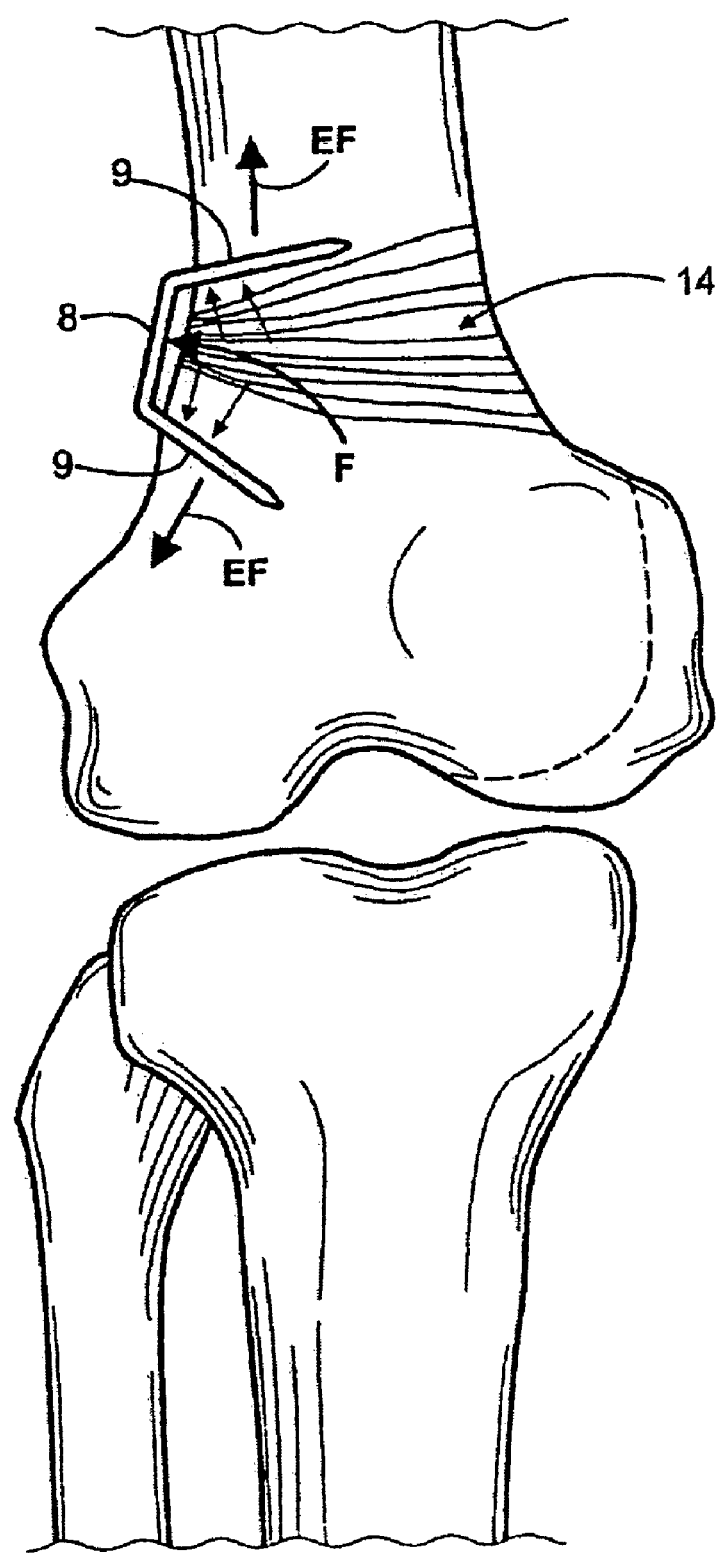
FIG. 7 shows a diagrammatic side elevation view of the femur head of FIG. 6 after a period of time has passed from the surgery, with the staple diverged into a substantial normal position, as shown in a resting position in FIG. 5, but completely inserted into bone and not slipped out as it occurs in the prior art (FIG. 4)

Also according to the invention, a method is provided for installing staple 7 into an upper bone 10 as shown in FIGS. 6, 7. FIG. 6 clearly shows that the upper bone has an abnormal bottom right side which is smaller than the bottom left side, this causing the bottom bone of the limb extending out of a normal axis and forming an angle with the axis of the upper bone 10. If both sides of the bottom end of bone 10 would be normal, having the same size, the bottom bone would join bone 10 along the same common axis. According to the method, staple 7 is provided with the legs normally diverging from each other, a compression force P is applied to the legs until bringing the same to a desired relative position, preferably a substantially parallel position. To bring the legs into a parallel relationship, the staple, if made of nitinol, may be cooled at a temperature of 0°, for example. Once in this position the staple may be nailed into the bone with at least one leg nailed at each side of abnormal epiphyseal plate 11, whereby the staple will be retained into the bone with the legs exerting an expansion force over the epiphyseal plate while the cross bar will exert an arrest or suppression effect on a periphery 12 of the epiphyseal plate.

Therefore, when the staple is introduced into the bone with each leg at each side of the epiphyseal plate under a compression force bringing the legs to be closer than in a normal position the legs exert a expansion force EF for lengthening the epiphyseal plate while cross bar 8 remains unaltered, that is non deformed, keeping its normal length thus forming a tether for periphery 12 of the epiphyseal plate. This causes the epiphyseal plate to growth around a growing focus F defined at a central region of periphery 12. FIG. 7 clearly illustrates the growth of plate 11 around focus F, thus showing that plate 11 is prevented from growing only at the periphery thereof, arrested by cross bar 8 while the remaining portion 13 of plate 11, namely most part of plate 11, not only is allowed to growth but is induced to growth by the expansion force of spring legs 9. This growing is larger at the right side of plate 11 as indicated by reference number 14. The phantom line at the right side of the bottom end of bone 10 indicates the abnormal former profile of the bottom as appearing in FIG. 6. The right side of the bone has now grown and the bones are normally aligned.

As stated above, the staple may be nailed into the bone and this nailing step may be carried out by drilling orifices in the bone, one orifice for receiving one leg of the staple. Alternatively, the step of nailing may comprise nailing the staple directly into the bone by hammering the staple on the bone.

According to another embodiment of the invention, the staple shown in FIGS. 8, 9, also named in this application as abutting staple, is designed to prevent the surface bone or the cartilage plate remaining under the cross bar from being damaged from the staple. The staple of FIG. 8, indicated by general reference 15, may be manufactured from a resilient or not material, such as chrome-cobalt alloy, cold-worked 316 SS, medical grade, stainless steel, titanium, nitinol, etc.

Staple 15 comprises a bridge or cross bar 16 and legs and is preferably for use in correcting bone deficiencies, either angular or length abnormalities, by controlling the growth of the epiphyseal plate.

Cross bar 16, according to another teaching of the invention, extends beyond a corner joint 18 wherein the bridge is connected to the legs. Thus, stop means 19 are defined in the corner for abutting the bone when the staple is hammered or nailed through other way to the bone level. In addition, the cross bar defines an arc shape (FIG. 8) extending between the legs and at a level higher than the stop means, whereby when the staple is installed into the bone the arc shaped cross bar remains spaced apart from the bone surface and, preferably from the epiphyseal plate. Cross bar 16 is curved like a beam knee with the highest part thereof at a central point of the bridge.

Preferably, the stop means comprises a shoulder as shown in FIG. 8 or, alternatively, may comprise a shoulder 19, shown in FIG. 9, which shoulder is being curved by means of a notch 20 to prevent stresses concentration. In addition, the stop means, and preferably shoulder 19, forms reinforcing means at each connection between the legs and the cross bar, thus making the staple work like a reinforced staple. The reinforcing means operate o oppose any diverging movement of the legs away from each other. The fact that the reinforcement is defined outside the legs, namely not between the legs as in the prior art staples, prevents the bone or the cartilage plate between the legs from being damaged by any reinforcement. When used spanning across a growth plate, stop means 19 located a level lower than the bridge, prevents the bridge from entering into contact with the growth plate.

Also according to the invention, a method is provided for installing bone staple 15 into a bone for correcting bone deficiencies by controlling the growth of the epiphyseal plate. The staple is provided placed in the bone with the cross bar spanning across the epiphyseal plate, and the staple is nailed into the bone with at least one leg nailed at each side of the epiphyseal plate, whereby stop means 19 abut against the bone at each side of the epiphyseal plate and the arc shaped cross bar remains spaced apart from the epiphyseal plate.

The nailing of the staple may comprise drilling orifices in the bone for receiving the legs of the staple. Alternatively, the staple may be directly nailed into the bone by hammering the staple.

According to a further embodiment of the invention, the staples shown in FIGS. 10, 11, also named screw staples, are designed to prevent the slipped out thereof from the bone. The inventive bone staple is preferably designed for repairing bones and correcting bone deficiencies, and comprises a body forming a cross bar 21 and at least two legs 22 extending from the cross bar, wherein each leg includes integrating means 23 preferably comprising at least one helical thread designed for anchoring into the bone. In addition, the cross bar is designed for being easily cut by means of any medical tool available at any operation room. The inventive design of osseous anchoring enhancing means 23 permits that, once the bone deficiency is overcome and the staple is osseous anchored the cross bar is cut and each leg is independently unscrewed and removed from the bone.

Osseous anchoring means may be applied to any kind of staple, such as those of FIGS. 5 and 8, 9. As an example, FIG. 11 shows means 23 as applied to the legs of a staple 26, for example a staple according to FIG. 9. While only one leg has been shown it is obvious that means 23 may be applied to all the legs of a staple. As it is better shown in FIG. 11, means 23 comprises a helical thread defining a screw in each leg of the staple. Preferably, thread 23 is defined by a longitudinal cross section comprising an upper flat plane 24 and a lower inclined plane 25, both planes helically extending around the corresponding leg.

Staple 21, including means 23 may be installed according to a method, also provided by the invention, for installing and removing bone staple 21, 26, for repairing bones and correcting bone deficiencies. The method comprises the steps of providing said staple and installing the staple by inserting the legs of the staple into the bone. Once the period of time enough for repairing the bone or correcting the bone deficiency has elapsed, wherein the staple legs are anchored, the cross bar may be cut in a location between the legs, and each leg is independently removed from the bone by gripping the portion cut from the bridge or the leg, and unscrewing the leg from the bone.

The installation of the staple into the bone may be carried out by nailing the staple into the bone, by drilling orifices in the bone for receiving the legs of the staple and nailing the staple into the orifices, or by directly nailing the staple into the bone by hammering the staple on the bone.

Figure 12:
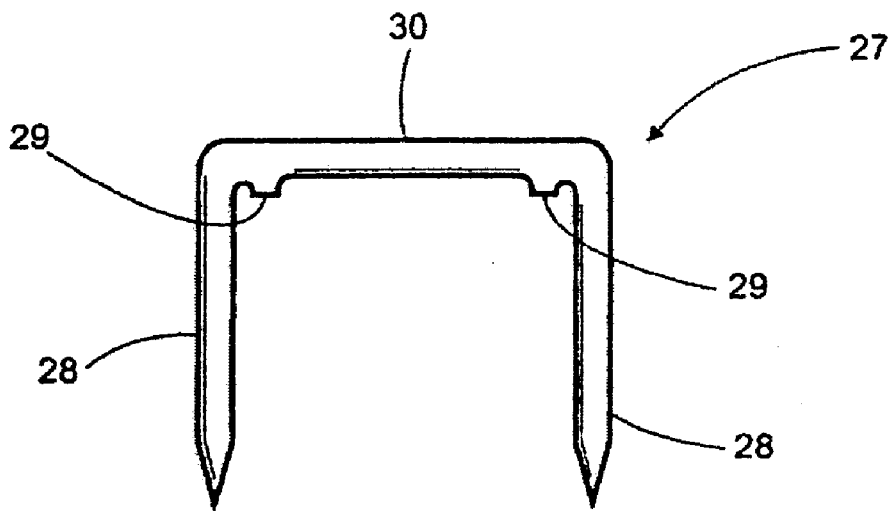
FIG. 12 shows a side elevational view of a bone staple according to a further embodiment of the invention.

According to FIG. 12, another embodiment of the invention is shown, staple 27 comprises stop means 29 located at an inner side of the staple, that is between legs 28. Stop means operate like stop means 19 of the staple shown in FIGS. 8 and 9. In order to prevent the stop means from contacting the growth plate, cross bar 30 will have a length enough to cross above the plate without entering into contact with the cartilage plate. Thus, stop means 29 will contact the bone at each side of the cartilage plate. In addition, stop means 29 will also operate to oppose to any diverging movement of legs 28 away from each other, against the expansion force of the cartilage plate. Therefore, staple 27, like staple 15, will operate like rigid staples.

Figure 13:
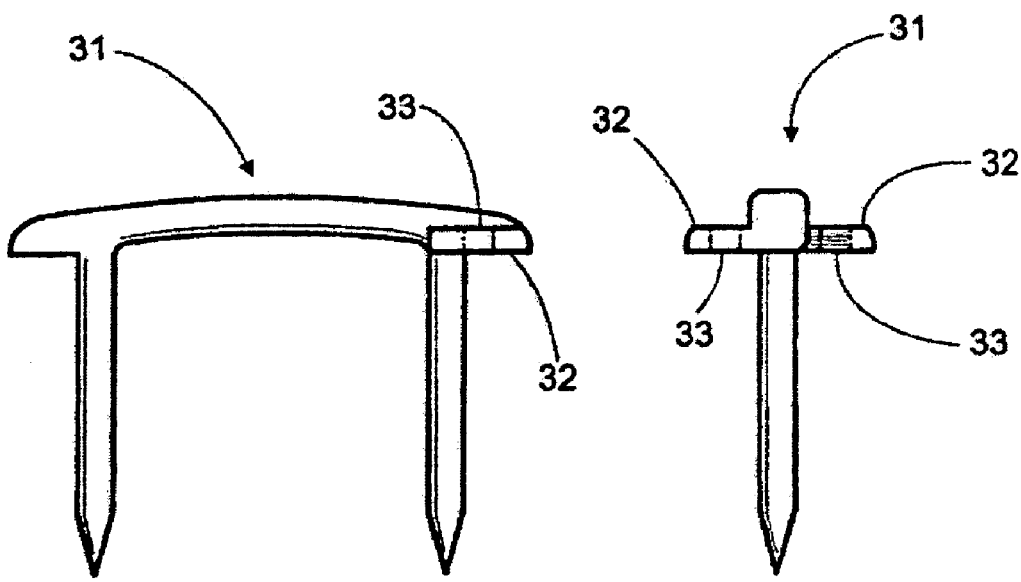
FIG. 13 shows a side elevational view of a bone staple according to another embodiment of the invention.
Figure 15:
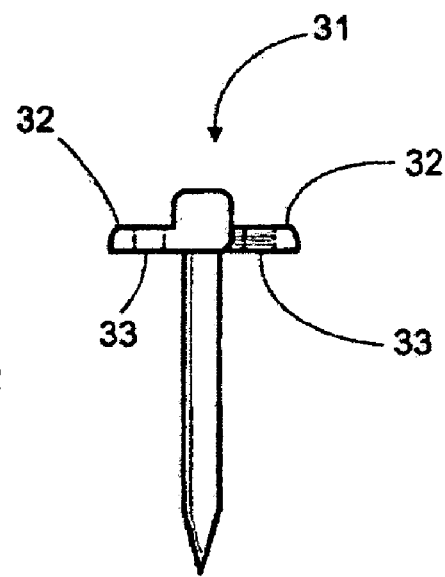
FIG. 15 shows an end elevational view of the bone staple of FIGS. 13 and 14.
Figure 14:
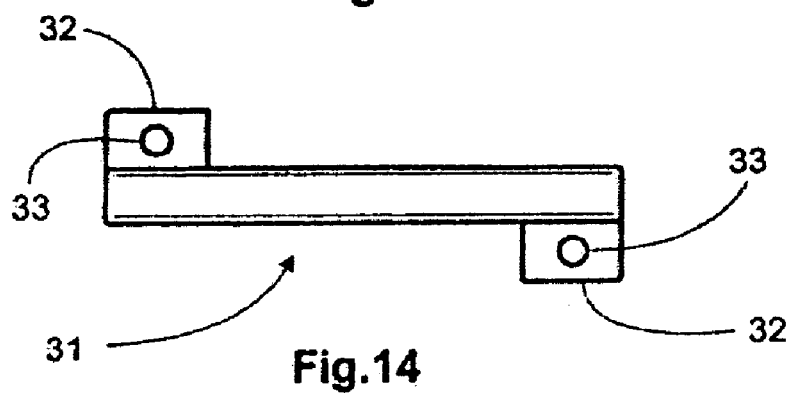
FIG. 14 shows a top plan view of the bone staple of FIG. 13.

Even according to another embodiment of the invention, FIGS. 13-15 show a staple 31 which may be used as a rigid staple or a resilient staple, expansion staple like the one of FIG. 5, depending of the material employed for manufacturing the staple. Furthermore, staple 31 may be provided with stop means like means 19 and 29, and screw means like thread 22 of FIGS. 10, 11. According to the invention, staple 31 is provided with retaining means 32 comprising ears at each side of the cross bar, each ear being designed to receive a fastening means, like a screw, not illustrated, passing through orifices 33. This alternative staple, may be advantageously employed in correcting spine disorders, by fixing the staple into vertebrae.

Depending on the use thereof, the staple of FIG. 12-15 may be installed into a bone by the methods already disclosed in connection to staples of FIGS. 5-11. Also, according to the application, staples of FIGS. 8-15 may be for angular correction or for length correction, thus applied at unilateral location or at uniform spaced apart locations respectively, and may be made of memory shape material, for expansion purposes, or made of rigid materials for compression or suppressing purposes.

According to even a further aspect of the invention, the inventive staple may comprise a simple rod made at least partially of a shape memory material such as a shape memory alloy like Nitinol (NiTi) and the staple, together with an also inventive method, is provided to correct a spinal column that is curved out of its natural curvature and has at least one concave side and at least one convex side. As it is shown in FIGS. 16 and 17, a spinal column affected by an abnormal curvature is indicated by general reference number 34 with the convex side and the concave side indicated by 35 and 36 respectively. The concave and convex side may occur at any side of the column, in other words the column may be deformed in the anterior-posterior direction or a lateral or diagonal direction, therefore, the view of FIGS. 16 and 17 are only examples of abnormal curvatures in any direction of the spine.

According to the inventive method, any distraction implant according to the present invention may be employed, and particularly the exemplified implant 37 is made of a shape memory material, such as a biocompatible steel, stainless steel, steel alloy, nitinol (NiTi), and the like. The implant has a central portion 38 and at least two opposite legs 39, and at least the legs are capable of adopting several shapes or positions, particularly a first shape, in a memorized state, and a second shape, in a deformed state. The legs extend diverging from each other in said first shape, this is in the memorized shape, as it is shown in FIGS. 3, 4, 5, 7, 17 and 22. If made of nitinol, the staple is thermally treated to settle a temperature range, for example, from about 35° to about 45°, at which temperature the shape of the staple is memorized with the legs in a diverging pattern to exert a distraction force when deformed out of its memorized shape.

Figure 23:
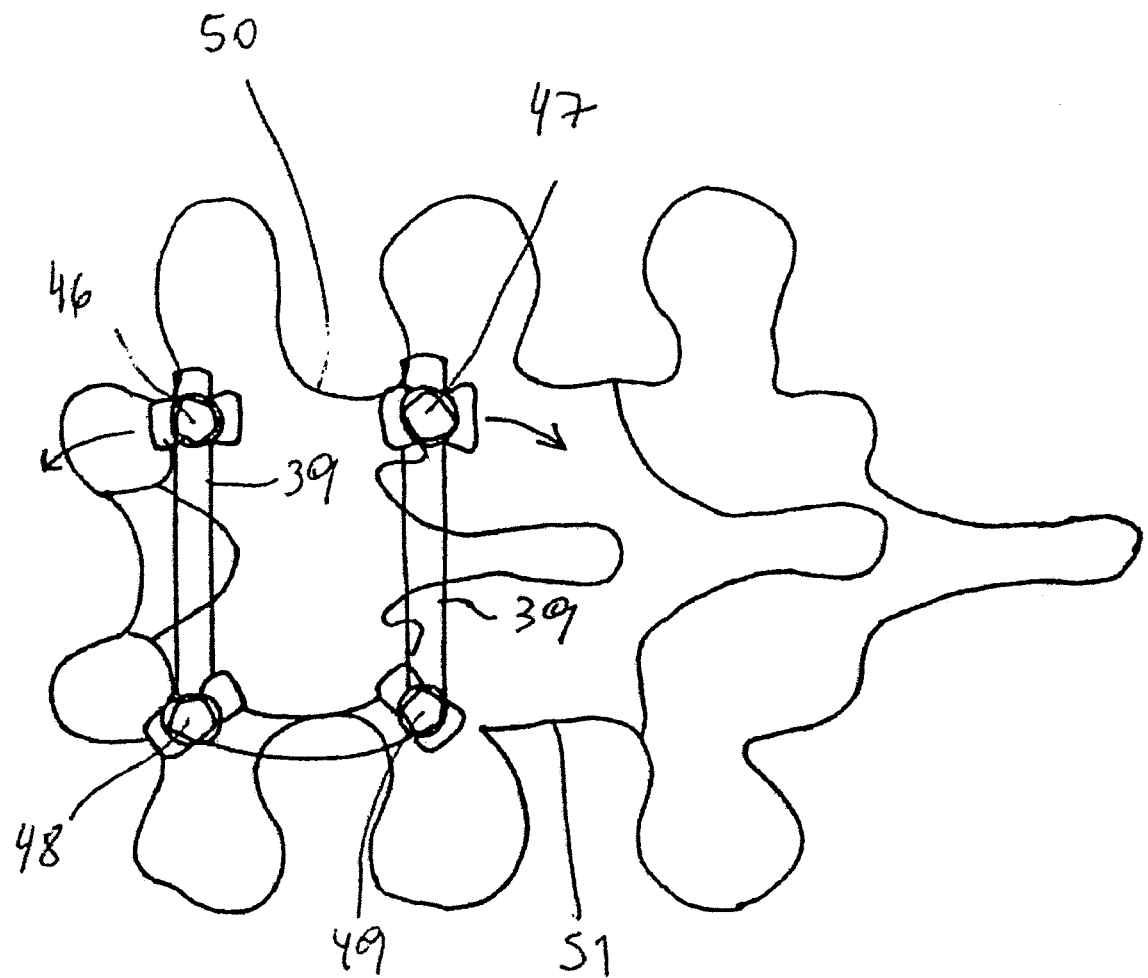
FIG. 23 is a posterior elevation view of a spinal column having a staple according to another embodiment of the invention, in its deformed status or shape, connected to two proximal vertebrae by four trans-pedicular screws.

The implant is brought to a deformed shape, with the legs parallel to each other for example, in order to connect the legs to the walls of two proximal vertebrae, as shown in the embodiment of FIG. 23, or to insert legs 39 into the vertebrae as shown in FIGS. 16-22. The implant may be deformed into said second shape by applying a compression force before connecting or implanting the staple or, if nitinol is employed, by cooling the implant at a temperature preferably between about −5° and about 0°.

With the staple deformed to the desired shape for facilitating implanting, the distraction implant or staple is implanted in convex side 35 by connecting one leg of the implant to one 40 of two proximal misaligned vertebrae and the other leg of the implant is connected to the other one 41 of the proximal vertebrae with central portion 38 extending, at the convex side, over corresponding epiphyseal plates 42, 43 of each proximal vertebrae. According to the invention, the legs 39 extend in a manner that at least a portion thereof, preferably distal portions 44, are placed close to concave side 36 when connected to the vertebrae. Thus, the legs are fixed to the vertebrae in the deformed state, see FIG. 16, with the legs exerting a distraction force, indicated by the arrows, over the epiphyseal plates 42, 43 of the vertebrae at said concave side. In this embodiment or any anyone of the other embodiments disclosed in this description, the legs of the implant may inserted into the vertebrae by first drilling an orifice in each vertebra and then inserting each leg into a corresponding one of the orifices or the legs may be nailed into the vertebrae according to any known technique.

As stated above, if the implant is made of nitinol, said first shape is set at a first temperature, between about 35° and about 45°, that is a temperature range including a normal temperature of the spinal column, and said second shape is determined at a second temperature lower than the first temperature, preferably between about −5° and about 0°. The heating of the staple to said first temperature may be made by the simple contact of the staple with the corporal temperature or by a heated saline solution, or by using low voltage electrical current, direct or percutaneous ultrasonic waves, and general high frequency waves concentrated into the staple.

End plate or epiphyseal plate 42, 43 is the place where longitudinal growth of the spine takes place. Plate 42, 43 has a circular ring that contributes to the increase in the size of the vertebral body and the end plate is similar to the physis of the long bones, therefore, for the purposes of this description, end plate and epiphyseal plate will be used indistinctly.

In connection to curvature abnormalities, during the development of a scoliotic curve, while the body of the vertebrae remains with the normal shape, the deformity occurs at the intervertebral spaces. The Nitinol divergent staple allows the application of a traction force to the intervertebral space and particularly to the end plate of a vertebra. The proposed treatment would work on the intervertebral space and the end plates. The staple distracts the space where the tissues are being compressed, namely the concave side, and limits the future growth of the convex side through the compression exerted by the inextensibility of the bridge or central portion 38 of the staple.

While reference has been made to the method and staple actuating with the distraction force over the end plates, growth plates or epiphysis of the vertebrae, the invention also provides the application of the staple into only one vertebrae or bone that must be corrected in its curvature or properly aligned. As depicted in the bottom vertebrae of the spine shown in FIGS. 16 and 17, staple 52 is inserted with the central portion 53 placed against the convex side defined by the bone, namely the spinal column, and with legs 54 extending close to the concave side defined by the bone, in order to exert a distraction force preferably only at the concave side without affecting the natural growth at the convex side. The vertebra, however, may not be afflicted by an abnormal curvature in itself but the vertebra and/or vertebrae may be misaligned in the spinal column. Under this consideration, the spinal column is the deformed or abnormally curved bone, therefore the vertebra must be curved in order to compensate the misalignment and to correct the spine curvature. As shown in FIG. 17, vertebra 55 has been deformed into a trapezium shape with the larger base at the concave side to compensate the abnormality. With this method employed in the selected and desired vertebra or vertebrae the entire curvature abnormality of the spine can be corrected.

Figure 20:
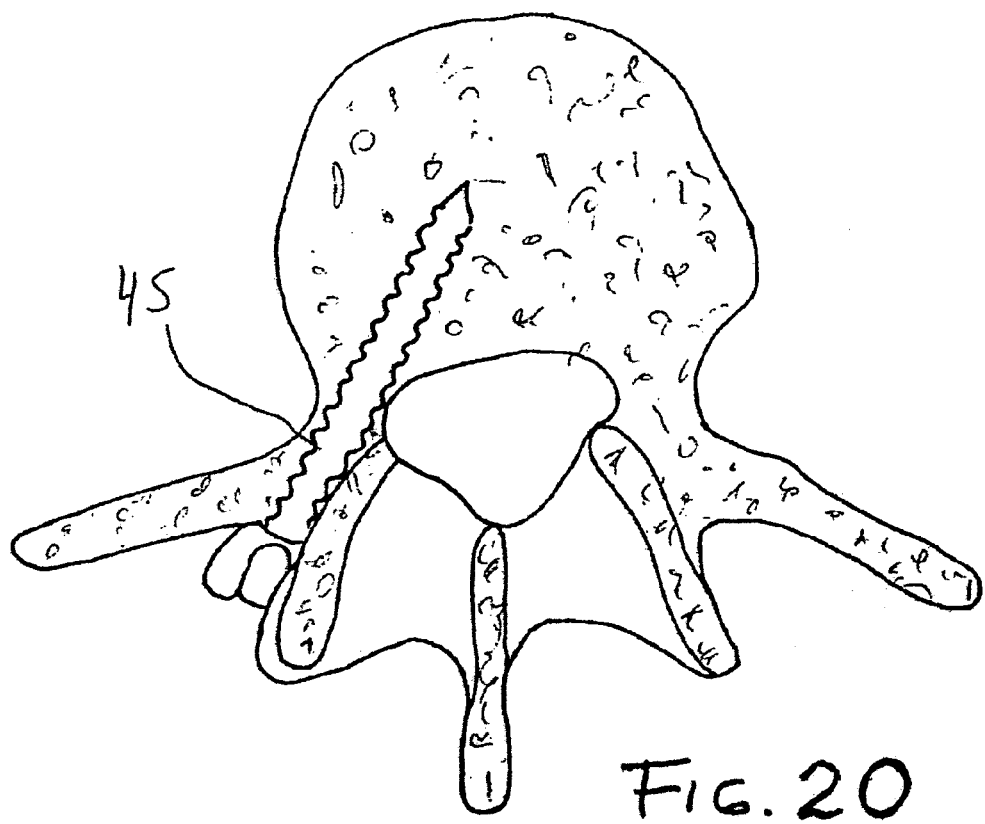
FIG. 20 is a cross section view of a vertebra similar to FIG. 19, having a hollow trans-pedicular screw implanted therein, with the screw ready to receive the leg of a staple of the invention.
Figure 19:
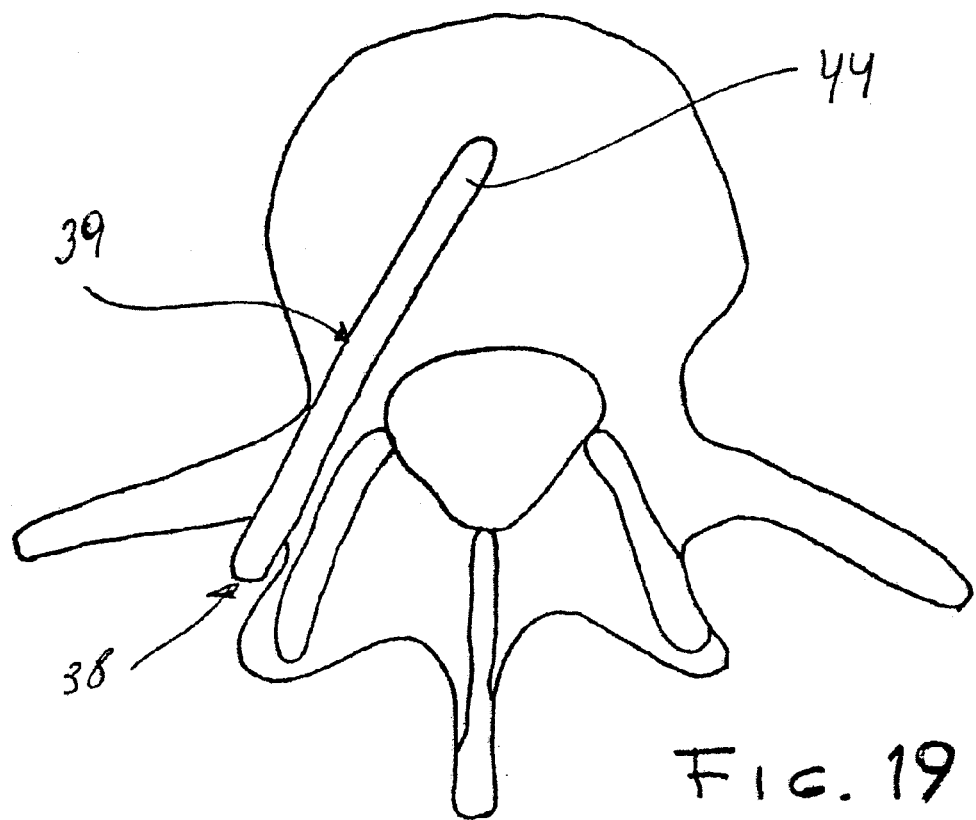
FIG. 19 is a cross section view of a vertebra having a staple implanted therein, through a posterior trans-pedicular approach, with only one leg of the staple being illustrated.
Figure 21:
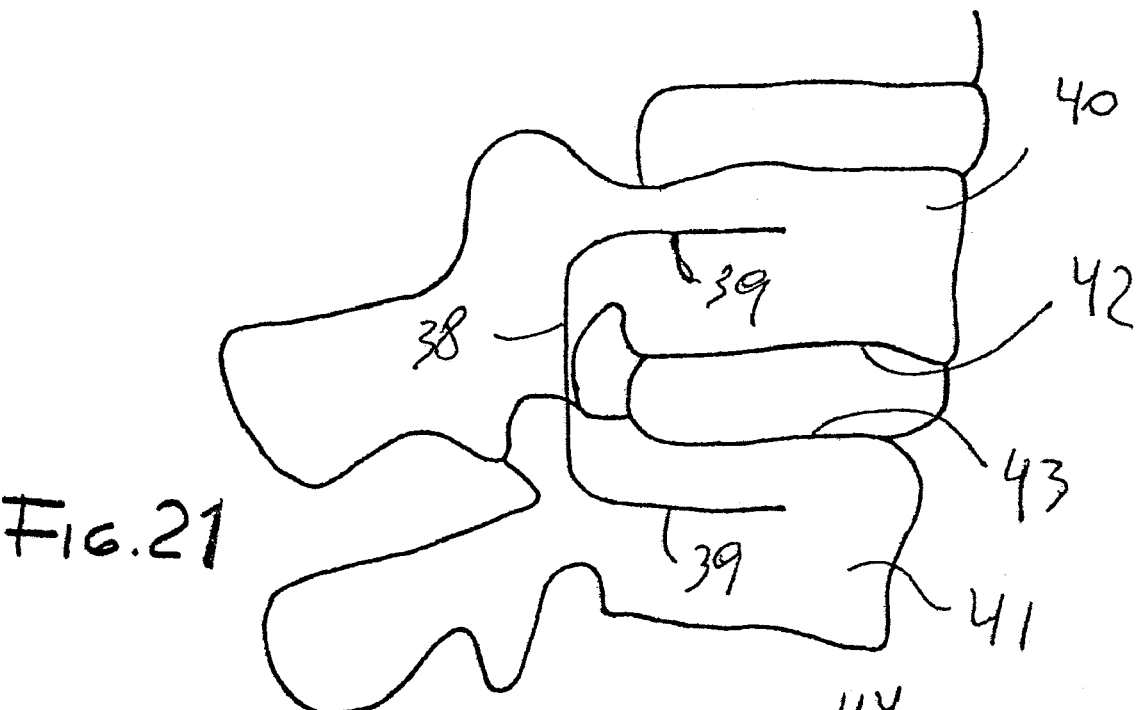
FIG. 21 is a side elevation view of a spinal column having a staple according to the invention, in its deformed status or shape, implanted in two proximal vertebrae through a trans-pedicular approach.
Figure 22:
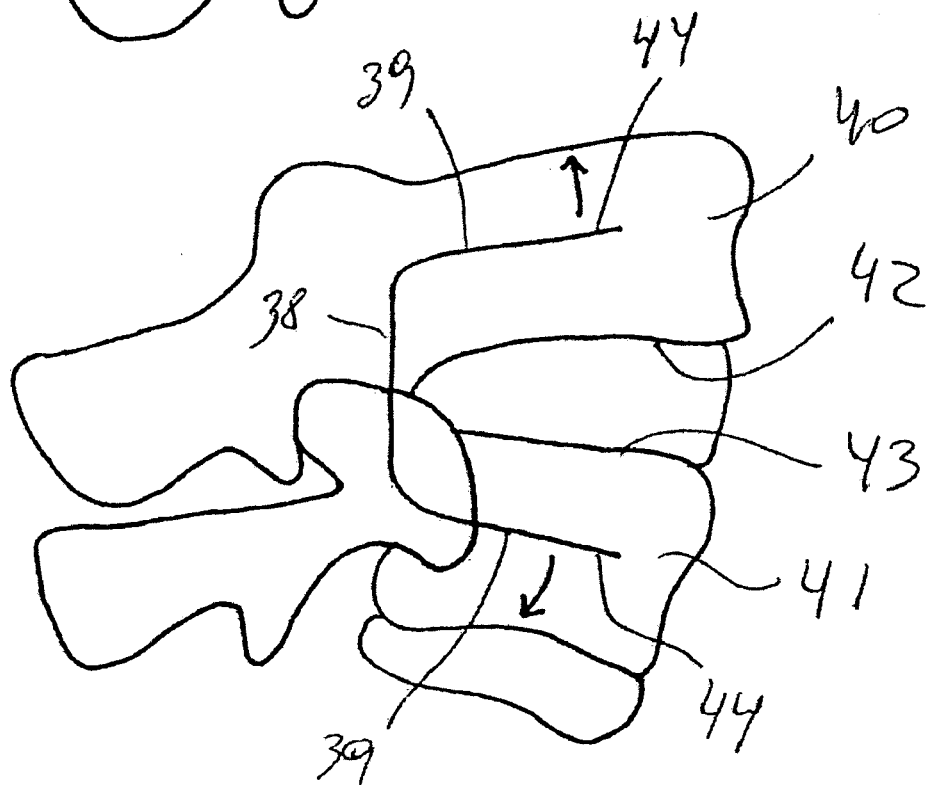
FIG. 22 is a side elevation view of the staple and spinal column of FIG. 21 as it is after a period of treatment time, with the staple in its memorized status or shape.

According to the method of the invention, the inventive implant may be implanted according to several approaches, such as by anterior surgical approach wherein the cooled Nitinol staple is deformed into the second shape to have the legs parallel and it is applied or connected to the body of two neighbor vertebrae, on the convex side of the curvature. The staple may be applied directly to the bone, or to a previously applied intermediate hollowed screw 45 imbedded in the vertebral body, as shown in FIG. 20.

Figure 18:
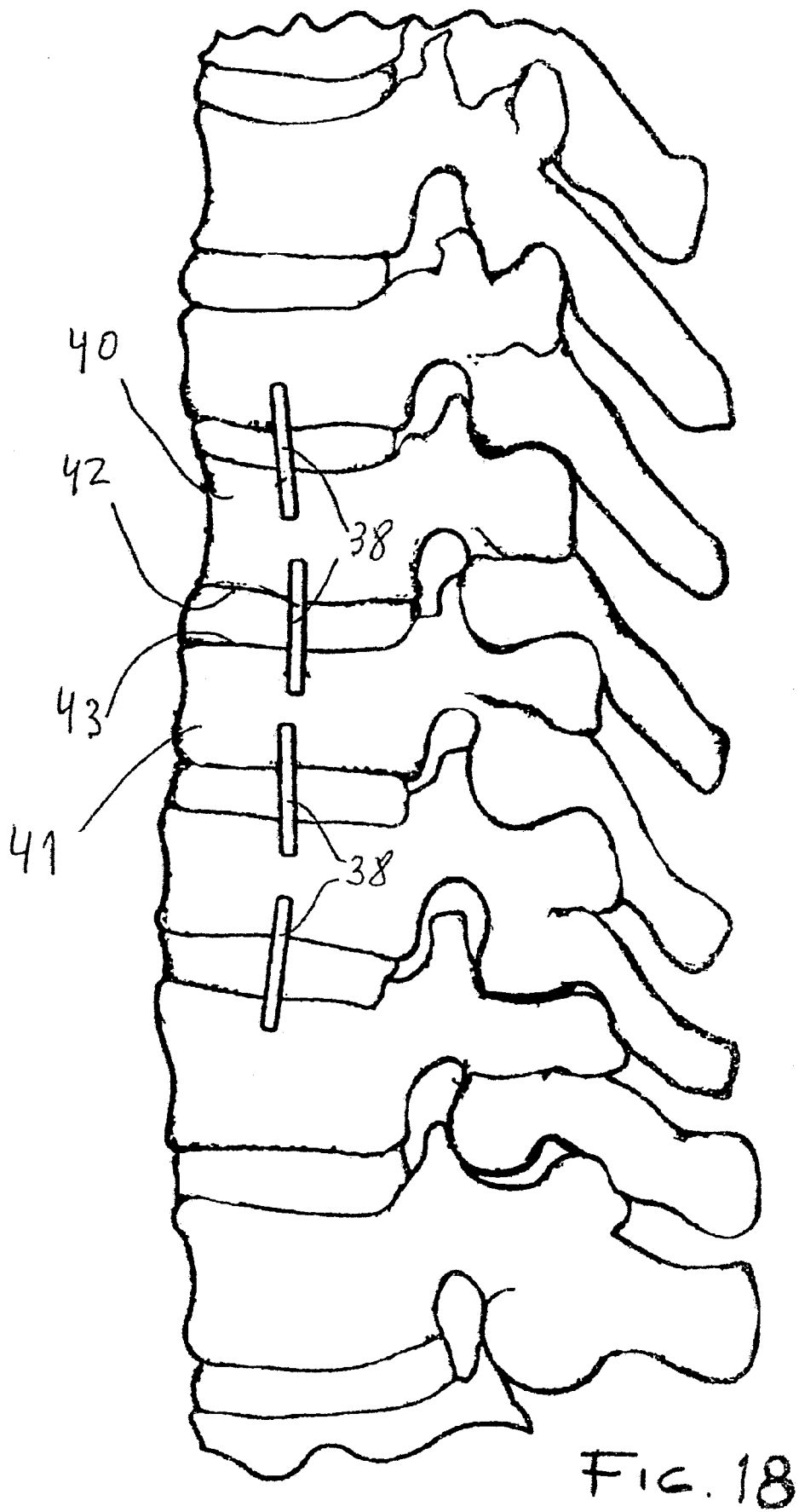
FIG. 18 is a side elevation view of the spinal column of FIGS. 16, 17, showing four staples implanted in five proximal vertebrae.

As shown in FIG. 18, one, two or more staples can be applied to each pair of vertebrae, according to the size of the patient and more than one pair of vertebrae can be operated upon if the curve is large. The staple can be applied more anterior if there is also a need to correct a lordotic (hypokyphosis) deviation, as it is found very frequently. The method and staple may be also applied to other disorders such as Kyphosis, that is the increase of the normally occurring posterior dorsal curvature of the spine, and Lordosis, that is the opposite deformity, the dorsal spine is abnormally straight or has a concavity where normally there is convexity. According to the specific deformity the staple will be connected to the vertebrae by means of a screw in a trans-pedicular approach, shown in FIG. 20, directly into the vertebrae through a trans-pedicular approach, shown in FIGS. 19, 21 and 22, or by a posterior surgical approach as shown in FIG. 23.

For the posterior surgical approach four hollow pedicle screws 46, 47, 48, 49, are applied to the four pedicles of two neighbor vertebrae 50, 51, reaching the vertebral body. A U deformed nitinol staple 37 is threaded through the four holes, not illustrated, of the screws in a manner that the straight branches of the U, namely legs 39, are threaded through the two screws of the proximal vertebrae, with the connecting bridge, namely central portion 38, of the staple is at one side, on the convex side of the curvature. Portion 38 goes from the screw on the convex side of one vertebra to the screw on the convex side of the other vertebra. When the nitinol reaches the transformation temperature, it will transmit a traction force to the screws and to the intervertebral space and the end plate, thus attempting to straighten the curve. Besides, as the connecting bridge of the staple can not be stretched, it shall act as a rein on the convexity when the end plates will attempt to continue with its physiological growth.

The kyphosis deformity can also be corrected by the present inventive method by applying a staple, on the left side of the vertebrae, through a posterior approach, to the pedicles of two neighbor vertebrae at the apex of the deformity and by applying another staple to the pedicles on the right side of the two vertebrae. This procedure can be used on two or more pair of vertebrae. The staple can be introduced in the bone through the pedicles, or fixed to an intermediate device as hollowed pedicle screws, such as screw 45, or screws 46-49, or well known pedicle hooks or laminar hooks, previously applied to the bone.

Alternative approaches or positions may be elected according to the needs, for instance, it is very frequently found that there is rotation component, besides the lateral curve, in all the scoliotic curves. In this situation, the staples may be applied, connected or inserted, obliquely regarding the plane of the intervertebral space. As the distraction force takes place, there will be also, a oblique force exerted on the intervertebral space, producing a rotating force between the neighbor vertebrae. Therefore, both deviations, namely lateral and rotation deviations may be corrected at the same time.

Also according to the invention, the staple may have several shapes, configurations and designs, as already disclosed above. For example, the inventive staple may define, when in said first shape, a rectilinear rod, a curved rod, a "U" rod, and generally legs 39 and portion 38 may form only one rectilinear design. Therefore, each leg may define an inner angle of between about 90° and about 180° with the central portion. In any case, according to the concepts of the invention, central portion 38 has a length longer than an intervertebral distance 52 defined between two proximal vertebrae at said convex side and each leg has a length enough to extend close to said concave side of the spine column, that is, portions 44 must be close to the concave side to exert the distraction force at this concave side without affecting the convex side. If made of nitinol, the staple may be made only partially of nitinol, for example only legs 39 may be of nitinol.

As an alternative, staples as shown in FIGS. 5 and 8-15 may be employed. If staples with enhanced retention into the vertebrae body are necessary or desired, the staple may be a distraction implant with each leg including a helical thread designed for anchoring by osseous integration into the vertebra, and the central portion may be designed to be cut whereby once the staple must be removed from the vertebrae, at the end of the healing period of time, the central portion is cut in a location between the legs, and the legs are removed from the vertebrae by gripping and unscrewing the legs.

For the purpose of this invention, the expression stating that the legs of the distraction implant extend in the second shape, means that the legs extend in a manner that at least part of their lengths are closer to each other as compared to the position they have in the diverging pattern at the first shape, whereby when in the second shape the legs will exert a force tending to adopt the diverging pattern of the first shape. Also, the expression that the legs extend close to the concave side of the spinal column means that the tips or distal ends or portions of the legs reach a zone of the vertebrae enough to exert a distraction effect in the concave side of the spinal column in order to correct the misalignment of the vertebrae.

As it will be apparent to any person skilled in the art, the methods and staples of the invention provides several advantages. The implanted staple or staples will not apply any abnormal pressure in the intervertebral space and the possible damage of the disk is prevented. The compressive pressure over the disk is a drawback related to many of the prior art methods, staples and procedures which apply a compressive staple to the convexity from the beginning of the treatment. The staples of the present invention are applied on the convex side of the spine, therefore the surgical procedure is much easier because all the important anatomical elements are displaced towards the concave side. The system of the invention also works both ways, by applying traction on the intervertebral space and on the end plate. This stimulates the formation of more cartilage and new bone. It would be an effect similar to the one applied by external spine braces where the distraction is applied externally to the curve through a three point pressure system.

The nitinol staple can have a thread made at both ends. It is convenient that the thread should be made as a buttress thread, with one side of the thread almost perpendicular to the long axis of the staple. This will add stability, to prevent the extrusion of the staple. As the staple will always keep the tendency to diverge, the crest of the threads and grooves of the buttress thread will be pressing against the bone, preventing the extrusion. It will also work as a stabilizing factor the fact that the new bone will be growing in the threads, as the Nitinol is a biocompatible metal alloy.

As the staples cross the intervertebral space, there is going to be motion at the bridge of the staple. The forces will be bending, extension, compression and torsion. As the nitinol has superelastic properties, it will be able to sustain its integrity through the course of the treatment and delay a fatigue breakage. If there is a need to remove the staple because the treatment is finished, the bridge can be cut, as stated above, with a wire cutter, and both halves could be removed by unscrewing each imbedded leg of the staple. The nitinol staple can have both legs angulated with any desired angle, but angles from 175° to 95° are the preferred ones. Various materials with shape memory properties or elastic properties are contemplated for the body, including gels, elastomers, visco-elastic-gels or plastics, shape memory alloys, other biocompatible materials and combinations thereof.

While it may not be specifically illustrated, it is remarked that the features of each of the staples illustrated and disclosed herein are capable of being combined selectively or entirely for specific applications. For example, anchoring means 22 may be provided in any of staples 5, 15, 27 and 31, and the diverging-legs design of FIG. 5 may be applied to any of the remaining staples as long as the staple is made of a resilient material or shape memory material or alloy.

While preferred embodiments of the present invention have been illustrated and described, it will be obvious to those skilled in the art that various changes and modifications may be made therein without departing from the scope of the invention as defined in the appended claims.

I claim:

1. A method for modifying the curvature of at least one vertebra that defines at least one concave side and at least one convex side of a spinal column, the method comprising:
   providing a distraction implant made of a shape memory material and having a central portion and at least two opposite legs, with each of the at least two legs having a distal end, and with the implant having a first shape, in a memorized state, and a second shape, in a deformed state, wherein the legs extend diverging from each other in said first shape;
   bringing the implant into said second shape; and
   implanting the distraction implant into the at least one vertebra by inserting the legs of the implant into the at least one vertebrae through the convex side of the spinal column defined by the at least one vertebra up to a position that the distal end of each leg is close to the concave side of the spinal column, with the legs extending in the second shape, whereby the legs in the deformed state, are fixed to the at least one vertebra and exert a distraction force in said concave side of the spinal column,
   wherein the distraction force exerted by the distraction implant allows the at least one vertebra to expand, at the concave side of the spinal column, in the direction of the distraction force to straighten the spinal column.

2. The method of claim 1, wherein the step of implanting the distraction implant in the convex side of the spinal column comprises inserting one leg of the implant to one of two proximal misaligned vertebrae and the other leg of the implant to the other one of the proximal vertebrae with the central portion extending, at the convex side of the spinal column, over corresponding epiphyseal plates of each proximal vertebrae, whereby the legs, in the deformed state, are fixed to the vertebrae and exert a distraction force over the epiphyseal plate of the vertebrae at said concave side.

3. The method of claim 2, wherein the implant is fixed to walls of the vertebrae by screws.

4. The method of claim 2, wherein the implant has said first shape at a first temperature that is a normal temperature of the spinal column and said second shape at a second temperature lower than the first temperature, and the implant is brought to said second shape by bringing the implant to said second temperature, and wherein the implant is warmed up to the first temperature, in contact with the vertebrae, whereby the legs tend to recover their first shape and exert a distraction force at the concave side in the proximal vertebrae.

5. The method of claim 2, wherein the legs of the implant are inserted into the vertebrae by first drilling on orifice in each vertebrae and then inserting each leg into a corresponding one of the orifices.

6. The method of claim 2, wherein the legs are substantially parallel when in said second shape.

7. The method of claim 2, wherein the implant defines a rectilinear rod when in said first shape.

8. The method of claim 2, wherein the implant defines a curved rod when in said first shape.

9. The method of claim 2, wherein the implant defines a "U" rod when in said first shape.

10. The method of claim 2, wherein each leg defines an inner angle of between about 90° and about 180° with the central portion.

11. The method of claim 2, wherein the implant is made at least partially of Nitinol.

12. The method of claim 4, wherein the first temperature is between about 36° and about 45° and the second temperature is between about −5° and about 0°.

13. The method of claim 1, wherein the step of providing a distraction implant comprises providing the implant with each leg including an helical thread designed for anchoring by osseous integration into the vertebrae, and the central portion being designed to be cut whereby once the staple must be removed from the vertebrae the method comprises the steps of:

cutting the central portion in a location between the legs, and removing the legs from the at least one vertebra by gripping and unscrewing the legs.

14. The method of claim 2, wherein the implanting step comprises nailing the staple into the vertebrae.

* * * * *